(12) United States Patent
Rahaman et al.

(10) Patent No.: US 8,357,205 B2
(45) Date of Patent: Jan. 22, 2013

(54) FEMORAL HEAD AND METHOD OF MANUFACTURE THEREOF

(76) Inventors: Mohamed Naushad Rahaman, Rolla, MO (US); Bhajanjit Singh Bal, Columbia, MO (US); Yadong Li, Suzhou (CN)

( * ) Notice: Subject to any disclaimer, the term of this patent is extended or adjusted under 35 U.S.C. 154(b) by 408 days.

(21) Appl. No.: 12/100,951

(22) Filed: Apr. 10, 2008

(65) Prior Publication Data

US 2008/0255674 A1  Oct. 16, 2008

Related U.S. Application Data

(60) Provisional application No. 60/922,611, filed on Apr. 10, 2007.

(51) Int. Cl.
*A61F 2/28* (2006.01)
(52) U.S. Cl. .................................................. 623/23.53
(58) Field of Classification Search ..... 623/22.11–22.39
See application file for complete search history.

(56) References Cited

U.S. PATENT DOCUMENTS

| | | | |
|---|---|---|---|
| 4,171,544 A | 10/1979 | Hench et al. |
| 5,336,465 A | 8/1994 | Matsunaga et al. |
| 5,879,404 A | 3/1999 | Bateman et al. |
| 6,682,567 B1 | 1/2004 | Schroeder |
| 6,881,229 B2 | 4/2005 | Khandkar et al. |
| 2005/0090903 A1 | 4/2005 | Khandkar et al. |
| 2005/0273176 A1 | 12/2005 | Ely et al. |
| 2006/0184251 A1 | 8/2006 | Zhang et al. |
| 2006/0198943 A1 | 9/2006 | Kumar |
| 2007/0032877 A1 | 2/2007 | Whiteside |
| 2007/0255412 A1 | 11/2007 | Hajaj et al. |
| 2009/0187255 A1* | 7/2009 | Jani et al. ................. 623/23.53 |

FOREIGN PATENT DOCUMENTS

| | | |
|---|---|---|
| EP | 0410711 A1 | 1/1991 |
| EP | 1433443 A1 | 6/2004 |
| EP | 1679088 A2 | 7/2006 |
| WO | 2007121242 A2 | 10/2007 |

OTHER PUBLICATIONS

Hennig et al, Polyethylene (PE)-Abrasion Minimizing Ceramic and Metal Compound Hip Prosthetic Heads, Unfallchirurg, 1995, pp. 526-529, vol. 98, No. 10, English Translation, Abteilung für Unfallchirurgie, Universität Erlangen-Nürmberg, Germany.
Sodha et al, Concepts of the Modern Ceramic on Ceramic Total Hip Arthroplasty and Early Results, University of Pennsylvania Orthopaedic Journal, 2001, pp. 1-4, vol. 14.
Sales Brochure, Lineage Acetabular Cup System,Wright Medical Technology, Inc., © 2004, 10 pages, MH 542-901 Rev 02.04.

* cited by examiner

*Primary Examiner* — David Isabella
*Assistant Examiner* — Ann Schillinger
(74) *Attorney, Agent, or Firm* — Polsinelli Shughart PC (57) ABSTRACT

A femoral head made from a ceramic-metal composite having a multi-layered construction and related method of manufacture is disclosed. The femoral head includes an inner metal core bonded to a relatively thin ceramic outer layer that is used as the articulating surface with an acetabular cup during total hip arthoplasty. In another embodiment, an interface layer having a ceramic and metal mixture may be laminated between the inner metal core and the exterior ceramic layer.

3 Claims, 11 Drawing Sheets

FEMORAL HEAD AND METHOD OF MANUFACTURE THEREOF

CROSS REFERENCE TO RELATED APPLICATIONS

This application claims priority from U.S. provisional patent application Ser. No. 60/922,611, entitled "Ceramic-Metal Composite Femoral Head and Method of Fabrication" filed on Apr. 10, 2007.

FIELD

This document relates to the manufacture of a ceramic-metal composite, and more particularly to a ceramic-composite for a medical device.

BACKGROUND

Total hip arthroplasty, or total hip replacement, is an orthopedic procedure in which a surgically implanted device replaces a worn, damaged, or diseased hip joint. The surgically implanted device assumes the functions of the replaced hip joint, including support and joint articulation. The components of the surgically implanted device typically include an acetabular cup, a femoral head, and a femoral stem. The acetabular cup is a socket implanted into the hip that receives the femoral head having a smooth hemispherical surface adapted for articulation with the acetabular cup. The opposite end of the femoral head is attached to a fitting on the femoral stem, which is attached at its other end to the femur of a patient.

The implanted device should be biocompatible, structurally strong, tough, and wear-resistant. Further, the articulation between the acetabular cup and the femoral head should produce relatively low frictional engagement. These requirements, often conflicting, affect the choice of materials used to construct implanted devices. In particular, the femoral head should possess a hard and wear-resistant articulating outer surface, while also possessing tough, crack-resistant material properties in the region where the femoral head attaches to the femoral stem.

Therefore, a need exists in the art for an articulating structure to be used in an implanted orthopedic device that simultaneously possesses high hardness at the joint articulating surface, and high toughness where the structure joins to the underlying attachment structures.

SUMMARY

In one embodiment, a ceramic-metal composite is manufactured having an exterior ceramic layer with a relatively narrow thickness that may be bonded to a metal layer in a hot pressing process.

In another embodiment, a medical device may include a first articulating component made from a ceramic-metal composite with an exterior ceramic layer bonded to an inner metal core with the first articulating component adapted to engage a second articulating component. The first articulating component may have a hemispherical configuration in which the exterior ceramic layer is used as an articulating surface adapted to rotatably engage the second articulating component.

In yet another embodiment, the medical device may include a femoral head adapted to engage an acetabular cup for use in total hip arthroplasty. The femoral head may have a multi-layered body made of a ceramic-metal composite with a ceramic exterior layer as an articulating surface bonded to an inner metal core. The inner metal core may define an inner bore adapted to engage a femoral stem taper, while the ceramic exterior layer may be rotatably engaged to the acetabular cup in an articulating relationship.

In one embodiment, the femoral head may include a multi-layered body having a metal inner core bonded to a ceramic outer layer, the ceramic layer having an interface layer and an exterior ceramic layer. The interface layer may include one or more sub-layers made from a graded mixture of ceramic and metal materials.

In a further embodiment, a method for manufacturing an orthopedic implant component made from a ceramic-metal composite may include cold-pressing powdered metal and ceramic materials to form a compressed powder body, followed by hot pressing to consolidate and sinter the compressed powder body.

Additional objectives, advantages and novel features will be set forth in the description which follows, or will become apparent to those skilled in the art upon examination of the drawings and detailed description which follows.

BRIEF DESCRIPTION OF THE DRAWINGS

FIG. 11 is an SEM image showing the flexural fracture morphology of a laminated $Nb/Al_2O_3$ composite; and Corresponding reference characters indicate corresponding elements among the view of the drawings. The heading used in the figures should not be interpreted to limit the scope of the claims

DETAILED DESCRIPTION

Figure 1:
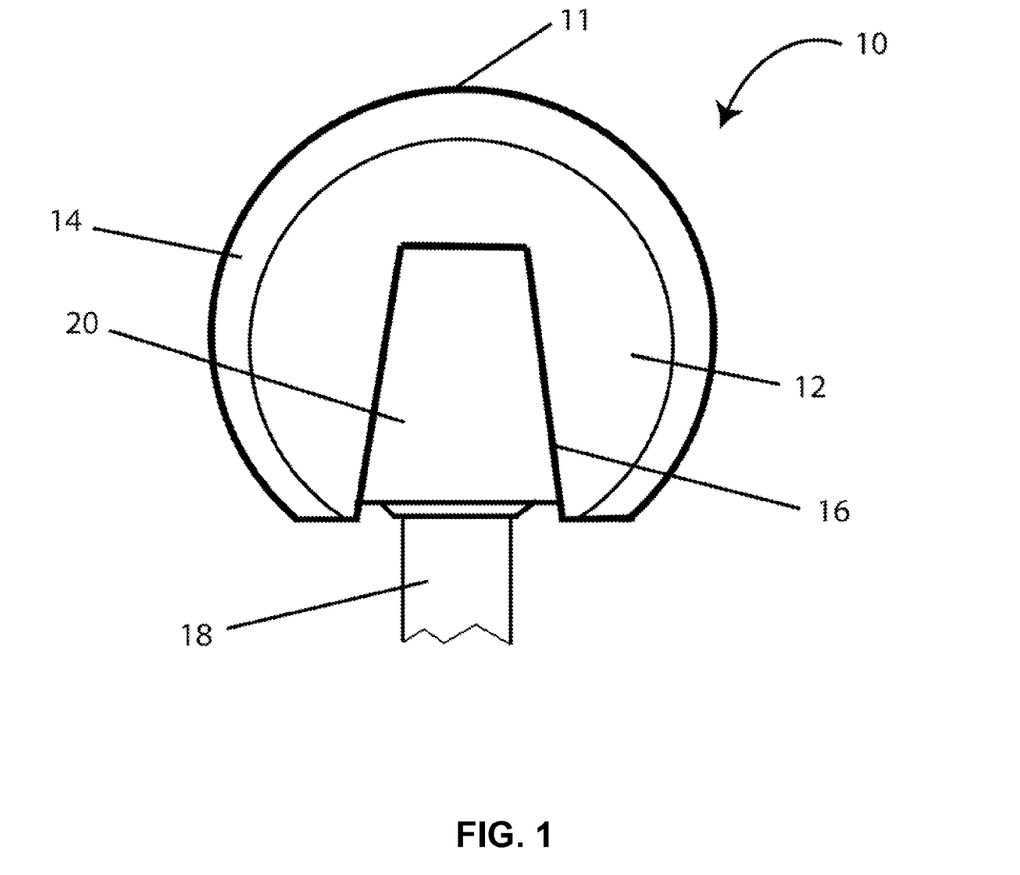
FIG. 1 is a schematic view of one embodiment of a femoral head having an inner core and an outer layer.

Referring to the drawings, an embodiment of the femoral head is illustrated and generally indicated as 10 in FIG. 1. The femoral head 10 includes a multi-layered body 11 having a generally hemispherical shape adapted to provide an articulating surface with an acetabular cup (not shown). As shown, the multi-layered body 11 may include a metal inner core 12 bonded to a ceramic exterior layer 14 having a generally hemispherical configuration. In addition, the metal inner core 12 defines a tapered bore 16 engaged to a metal taper 20 having a metal neck 18 that connects the femoral head 10 to a femoral stem (not shown) during a surgical procedure, such as total hip arthoplasty.

In one embodiment, the inner metal core 12 may be made of metal or metal alloys, such as Nb, Zr, Ti, Ta, Co, V, Cr, Al, alloys thereof, stainless steel, and combinations thereof. Any metal or metal alloy may be used to fabricate the metal core 12, so long as the material is biocompatible, bonds strongly to the ceramic material in the outer layer, and possesses adequate tensile strength and toughness to bear the loads experienced on the prosthetic joint during normal activities such as walking, running, standing, and jumping. The diameter of the metal inner core may range between about 10 mm and about 40 mm, and more preferably between about 25 mm and about 30 mm. The dimensions of the inner metal core 12 may be sized to assure that the metal material absorbs nearly all of the tensile stresses acting on the femoral head 10 via the metal taper 20, as determined by structural analysis techniques such as finite element modeling.

The exterior ceramic layer 14 is made of a ceramic material that may have a thickness ranging between about 200 microns and about 10 mm. For example, ceramic materials that may be used to manufacture the ceramic outer layer 14 include alumina, zirconia, chromium carbide, chromium nitride, silicon carbide, silicon nitride, titanium carbide, zirconium carbide, zirconium nitride, tantalum carbide, and tungsten carbide, pure or doped with other elements, composites of these ceramics containing one or more metal or ceramic phases, and combinations thereof. The ceramic exterior layer 14 may be fabricated from any ceramic material so long as the material is biocompatible, and possesses sufficient hardness and wear resistance to withstand the loads and wear on the femoral head 10 generated by normal activities such as walking, running, standing, and jumping. The thickness of the ceramic exterior layer 14 is dimensioned to ensure that adequate material exists to provide the needed structural integrity throughout the anticipated working life of the prosthetic femoral head 10.

In order to optimize the fabrication process, the metal material used to fabricate the metal core 12 may possess a similar melting point and coefficient of thermal expansion as the ceramic material used to fabricate the ceramic exterior layer 14. If the melting points of the metal and ceramic materials are significantly mismatched, the fabrication process may be constrained to occur at the lower melting point temperature, which may lengthen the fabrication time. If the coefficients of thermal expansion are significantly mismatched, residual stresses may form in the femoral head 10 during fabrication that may need to be ameliorated through the inclusion of an interface layer 13.

Figure 2:
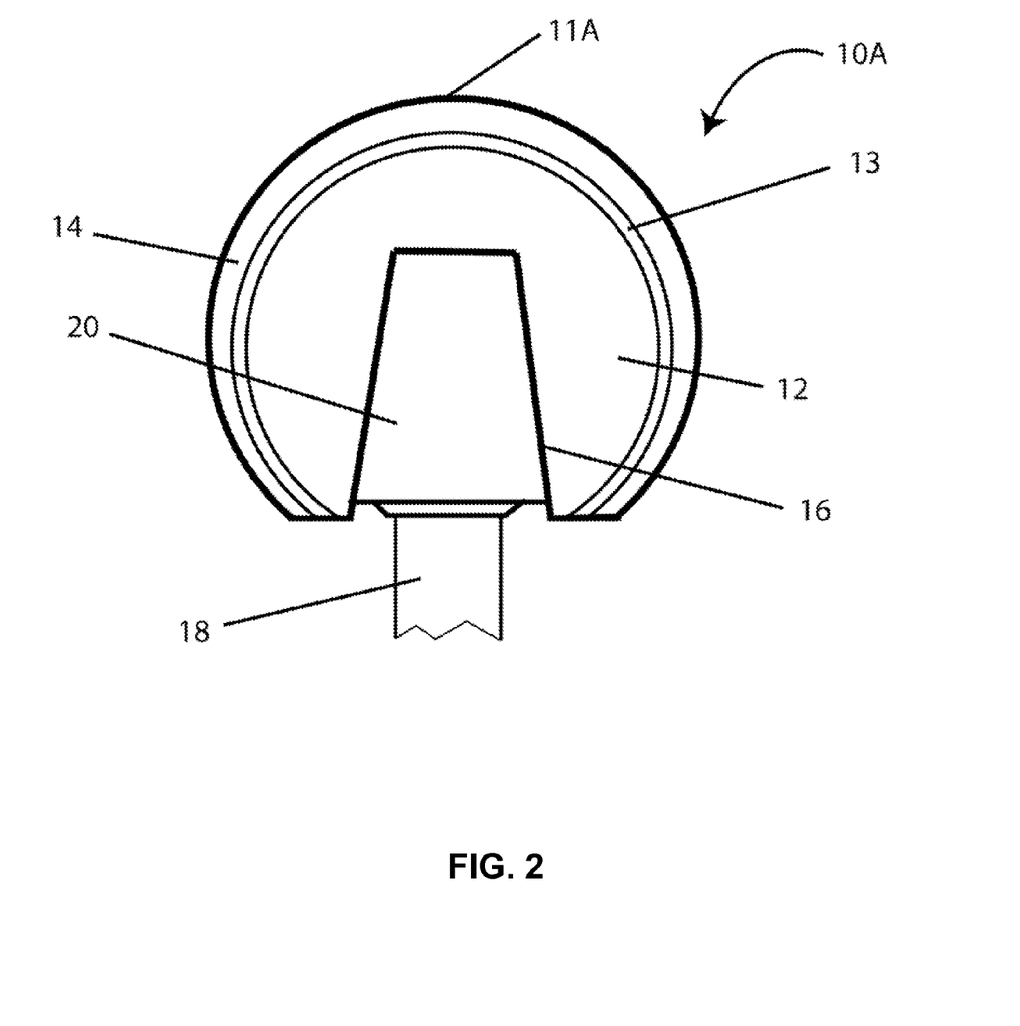
FIG. 2 is a schematic view of another embodiment of a femoral head having an interface layer between the inner core and the outer layer.

As shown in FIG. 2, another embodiment of the femoral head, designated 10A, may further include a multi-layered body 11A having an interface layer 13 made from a ceramic-metal composite that is bonded between the metal inner core 12 and ceramic exterior layer 14. The interface layer 13 may have a thickness ranging between about 0.5 mm and about 2 mm and may include one or more discrete sub-layers (not shown) bonded and laminated to one another. Further, the interface layer 13 may be made of a calibrated or gradient mixture of selected metal and ceramic materials.

The composition and thickness of the interface layer 13, in an embodiment, are selected to minimize the presence of residual stresses within the femoral head 10 resulting from the fabrication process. In addition, the interface layer 13 provides a more gradual transition between the hard, brittle exterior ceramic layer 14, and the softer, tougher metal core 12. The composition of the interface layer 13 or discrete sub-layers (not shown) may be mixtures of the metal and ceramic materials used for the metal inner core 12 and ceramic exterior layer 14, respectively. The fraction of the total volume of the interface layer 13 or discrete sub-layers may range between about 5% and about 95% of metal material, and may range between about 95% and about 5% of ceramic material. More preferably, the fraction of the total volume of the interface layer 13 or discrete sub-layers may range between about 10% and about 90% of metal material, and may range between about 90% and about 10% of ceramic material. In embodiments that include one or more discrete sub-layers in the interface layer 13, those layers with the highest metal content may be located nearest to the metal core 12. The number of discrete sub-layers may be minimized to reduce the cost and complexity of the fabrication process. The number of discrete sub-layers, if present, may range between about 1 and about 10 sub-layers, and more preferably between about 1 and about 5 sub-layers.

The overall diameter of the hemispherical femoral head 10 is sized to closely fit with the prosthetic acetabular cup of the prosthetic hip. The diameter of the femoral head 10 may range between about 20 mm and about 55 mm, and more preferably between about 26 mm and about 36 mm. The diameter of the tapered bore 16 is sized to closely fit the metal taper 20 of the femoral stem, thereby allowing the femoral head 10 to be force fitted to the metal taper 20 of the femoral stem. The diameter of the metal taper may range between about 10 mm and about 25 mm, and more preferably may range between about 10 mm and about 18 mm.

The femoral head 10 may be fabricated using powdered metal and ceramic materials using known fabrication techniques such as cold pressing and hot pressing. In an embodiment, a powdered ceramic mixture and a powdered metal mixture are assembled into a "green body" made of the powdered materials formed into the layers of the approximate dimension of the desired end product. The "green body" is then formed into the desired end product by known hot pressing processes.

In an embodiment, the powdered ceramic mixture may include the ceramic materials listed above such as alumina or zirconia, ground to a particle size of less than about 10 microns, and more preferably less than about 1 micron. The powdered ceramic mixture may also include ceramic conditioners such as magnesium nitrate, magnesium oxide, and other magnesium compounds, ground to a particle size of less than about 10 microns, and more preferably less than about 1 micron. The powdered metal mixture may include the metal materials listed above such as niobium or titanium, with a particle size of less than about 100 microns. The powdered metal mixture may also include a sintering additive such as cobalt powder with a particle size of less than about 100 microns.

The hot pressing processes used in various embodiments may include uniaxial hot pressing or isostatic hot pressing. In alternative embodiments, the ceramic exterior layer 14 may be fabricated using powder-based methods that utilize other known alternative consolidation methods, slurry-based methods, and vapor phase deposition methods such as CVD or PECVD.

Once the desired end product such as a femoral head 10 is provided, the exterior surface may be machined to its desired exterior contour using known techniques such as grinding or computerized diamond machining. In addition, the tapered bore 16 may be preformed or machined using known methods such as drilling or electrical discharge machining (EDM).

The ceramic-metal materials described herein may be used to fabricate the articulating components of orthopedic implants including prosthetic hips, prosthetic knees, prosthetic shoulders, prosthetic interphalangial joints, and prosthetic vertebrae.

EXAMPLES

The following examples illustrate various iterations of the present invention.

Example 1

Functionally Graded Alumina-Niobium Laminated Composites were Fabricated

To demonstrate the feasibility of fabricating alumina-niobium functionally graded composites in a hemispherical shape, the following experiment was conducted.

Commercially obtained ceramic and metal powdered materials were used to fabricate the hemispherical green bodies. Alumina ($Al_2O_3$) powder (Nanostructured & Amorphous Materials, Inc., 99.97%, 150 nm average particle size) was doped with 0.25% MgO by weight by combining the $Al_2O_3$ with magnesium nitrate ($Mg(NO_3)_2.6H_2O$, Johnson Matthey, Materials Technology, UK). The required quantities of the magnesium nitrate were dissolved in a small amount of water and then mixed with reagent grade ethanol. $Al_2O_3$ powder was added to the magnesium nitrate-ethanol solution, and the mixture was heated at about 80° C. and stirred to evaporate the solvents. The dried sediment was ground with an agate mortar and pestle for 30 minutes and then calcined at 600° C. for an additional hour. Prior to use, the calcined $Al_2O_3$ powder doped with 0.25% MgO by weight was ground again to a uniform consistency.

The metal powder was prepared by combining elemental niobium (Nb) powder (Cerac, 99.8%, −325 mesh) and a powdered cobalt sintering additive (Cerac, 99.9%, average particle size <4 μm). Cobalt powder was added to the niobium powder to make up 3% of the total weight of the mixture. The mixture was ground in an agate mortar for approximately one hour until a uniform powder consistency was achieved.

Due to small differences in the thermal expansion coefficients of alumina and niobium, interfacial residual stresses may be created between the two materials after the hot pressing process. To further reduce the thermal stress and to promote the interfacial thermal expansion coefficient matching between the two materials, powders for a series of transition layers were prepared. The transition layers consisted of the MgO doped alumina and Nb(3Co) mixtures with the following proportions of materials (expressed as % volume): 50% Nb(3Co):50% $Al_2O_3$, 30% Nb(3Co):70% $Al_2O_3$, and 10% Nb(3Co):90% $Al_2O_3$. All transition layer mixtures were ground with agate mortar and pestle for 30 minutes to achieve homogeneous mixtures of uniform consistency.

The laminated composite green bodies for the $Al_2O_3$ enwrapped Nb(3Co) hemispherical bearings were prepared by cold pressing the powders into a steel die in layers. The 100% Nb(3Co) powder was first pressed into a hemispherical shape, and then the transition layers were built up. The 50% Nb(3Co):50% $Al_2O_3$ was pressed onto the hemispherical shape in a layer thickness of about 1.5 mm to 2 mm, followed by the 30% Nb(3Co):70% $Al_2O_3$ powder, and then the 10% Nb(3Co):90% $Al_2O_3$ powder. A 1.5-2 mm layer of 100% MgO doped alumina powder was pressed on top of the transition layers, and the entire composite hemispherical body was subjected to cold isostatic pressing to increase the green body's density.

The green hemispherical body was transferred to a graphite die and surrounded with AlN powder for the hot pressing stage in an elevated temperature furnace with a graphite heating element in an argon atmosphere. Prior to heating, the furnace chamber was pumped down to below 100 mtorr of vacuum, then filled and refilled three times with 99.998% pure argon gas. The specimens were heated at a rate of 10° C.-15° C. per minute until a furnace temperature of about 1100° C. was achieved. The hemispherical body was then loaded with a uniaxial pressure at a rate of about 2 MPa per minute until a pressure of about 35 MPa was achieved. The furnace temperature during uniaxial pressure loading continued to increase up to a maximum of about 1400°-1450° C. The specimens were then cooled at a rate of about 10° C. per minute to a temperature of about 1200° C., and then the uniaxial pressure was slowly released from the hemispherical body down to a pressure of about 15 MPa. When the specimen had achieved a uniaxial pressure of about 15 MPa and a temperature of about 1000° C., the furnace was turned off and the uniaxial pressure was released from the hemispherical body.

After hot pressing, the outer surface of the hemispherical body was machined and polished. The Nb core was drilled using EDM machining to produce a central bore. The resulting $Al_2O_3$ enwrapped Nb(3Co) bearings had a spherical diameter of 32 mm with a tapered bore in the Nb metal core (Ø12×16).

The results of this experiment demonstrated the feasibility of fabricating a hemispherical bearing from a ceramic-metal composite materials using a technique of cold-pressing powdered materials in graded layers, followed by hot uniaxial pressing.

Example 2

The Microstructures and Interface Regions of Graded Alumina-Niobium Laminated Composite Materials were Characterized To demonstrate the feasibility of fabricating alumina-niobium functionally graded composites in a hemispherical shape, the following experiment was conducted.

Figure 3:
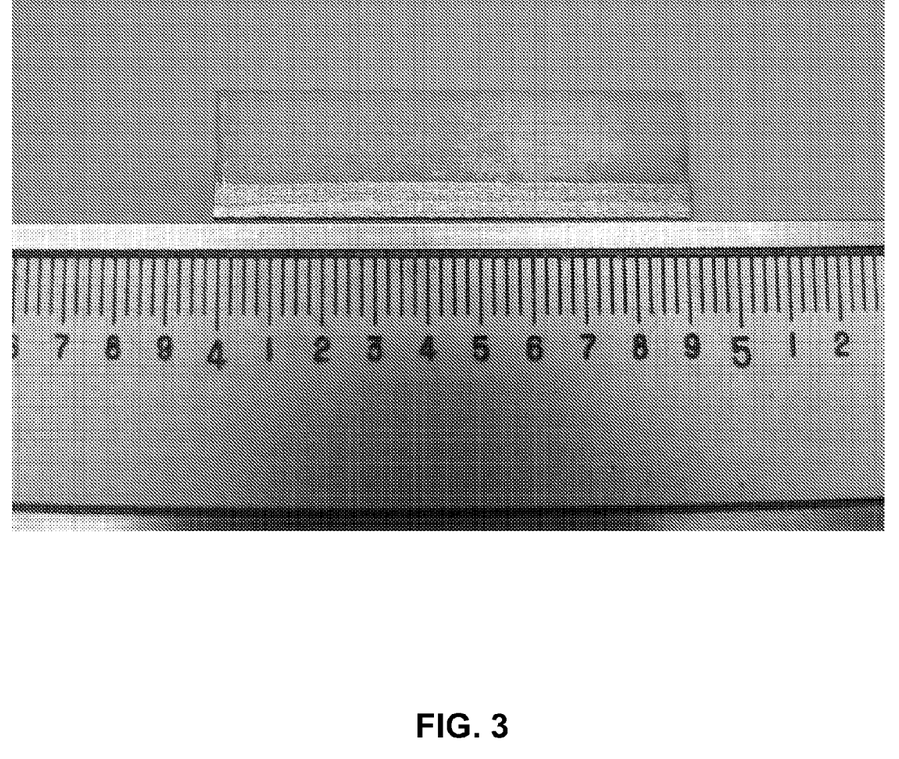
FIG. 3 is a cross-sectional photograph of an $Al_2O_3/Nb$ laminated composite with one interlayer ($Al_2O_3/Nb$-50 vol. % $Al_2O_3/Nb$)
Figure 4:
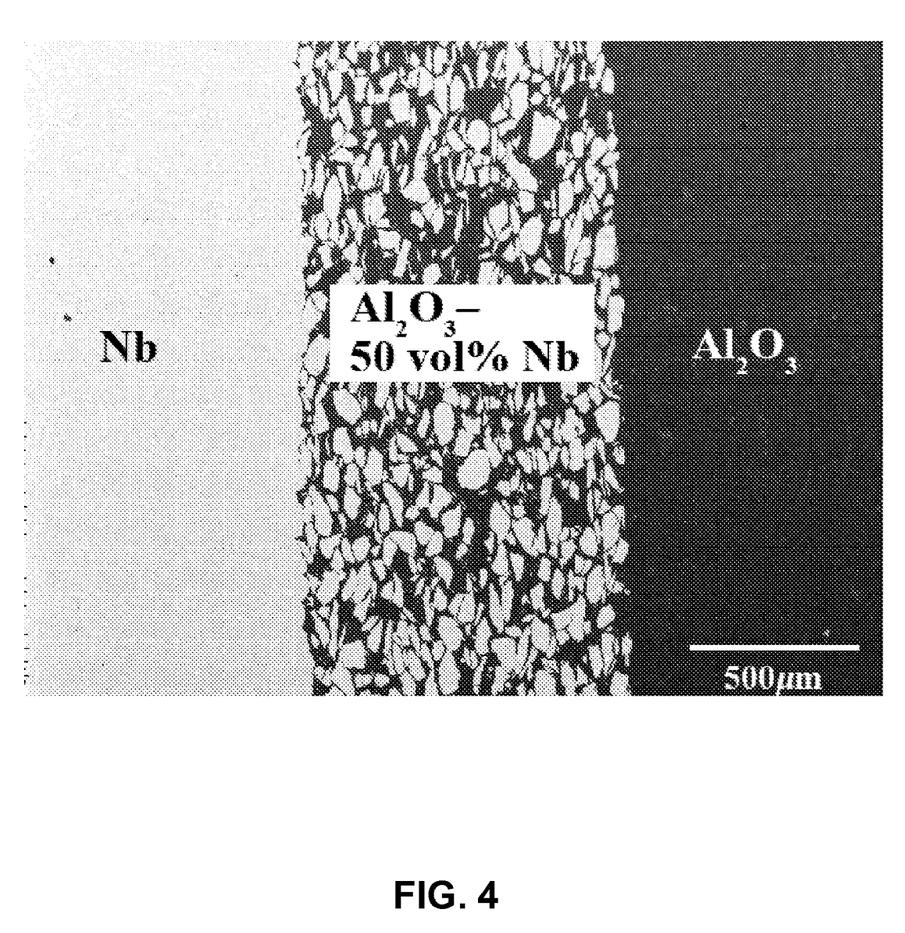
FIG. 4 is a cross-sectional SEM image of an $Al_2O_3/Nb$ laminated composite with one interlayer ($Al_2O_3/Nb$-50 vol. % $Al_2O_3/Nb$)

Alumina-niobium composite material samples fabricated in a disc shape using the methods described in Example 1 were sectioned by cutting along the axes of the disc using a diamond saw. The microstructures and interfaces of each of the layers of the composite bearing were investigated using scanning electron microscopy (SEM). FIG. 3 is a photograph of one resulting cross-section showing the darker alumina outer layer on top, and the lighter transitional layers and Nb inner layer on the bottom of the sample. FIG. 4 is an SEM image of the composite material sample, with one transition layer, showing good bonding at the interfaces between the layers. Further, the discrete occurrences of alumina particles, shaded black in the SEM image, and the Nb particles, shaded white, indicated that there was no apparent chemical reaction between the two composite components, and no third phase was formed.

Figure 5:
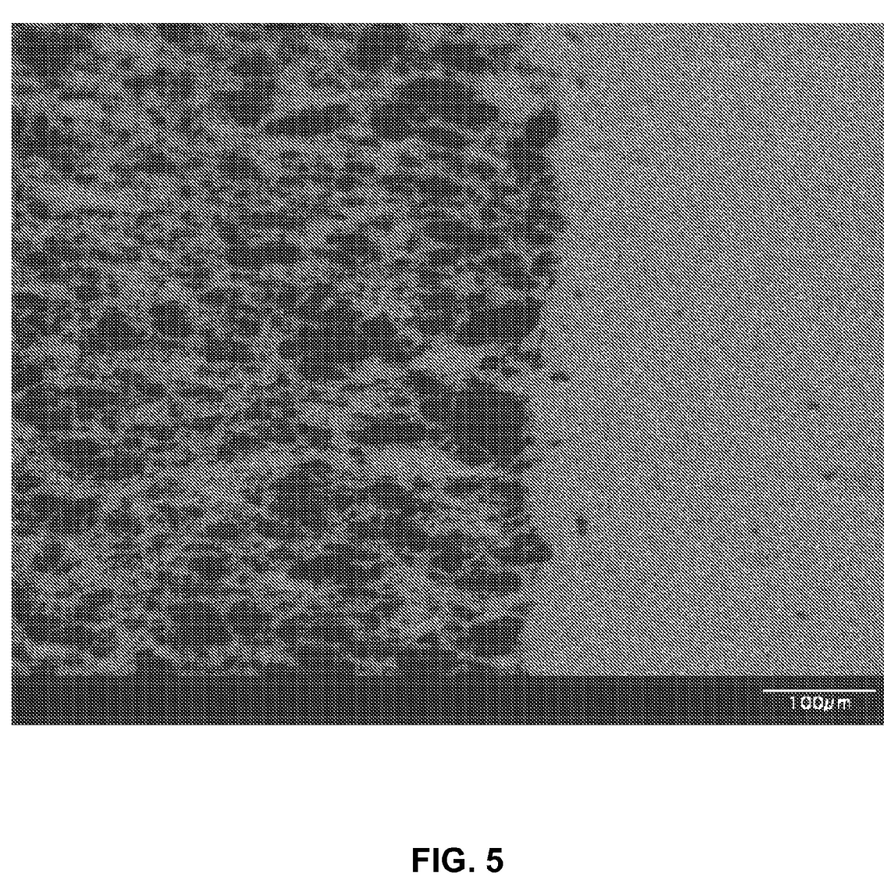
FIG. 5 is an Al (K) distribution map of an $Al_2O_3/Nb$ composite material as measured in Example 2.

To further characterize the transition between the layers of the composite material sample, concentration distributions of Nb and Al atoms in the sample were detected using an EDS surface scanning technique. FIG. 5 is an Al (K) distribution map of the composite material at the interface of the outer alumina layer and the underlying transition layer. The $Al_2O_3$ phase continuously distributed into the $Al_2O_3$—Nb transition layer, thereby indicating that strong bonding should be obtained between layers of the functionally graded $Al_2O_3$—Nb laminated composite.

Figure 6:
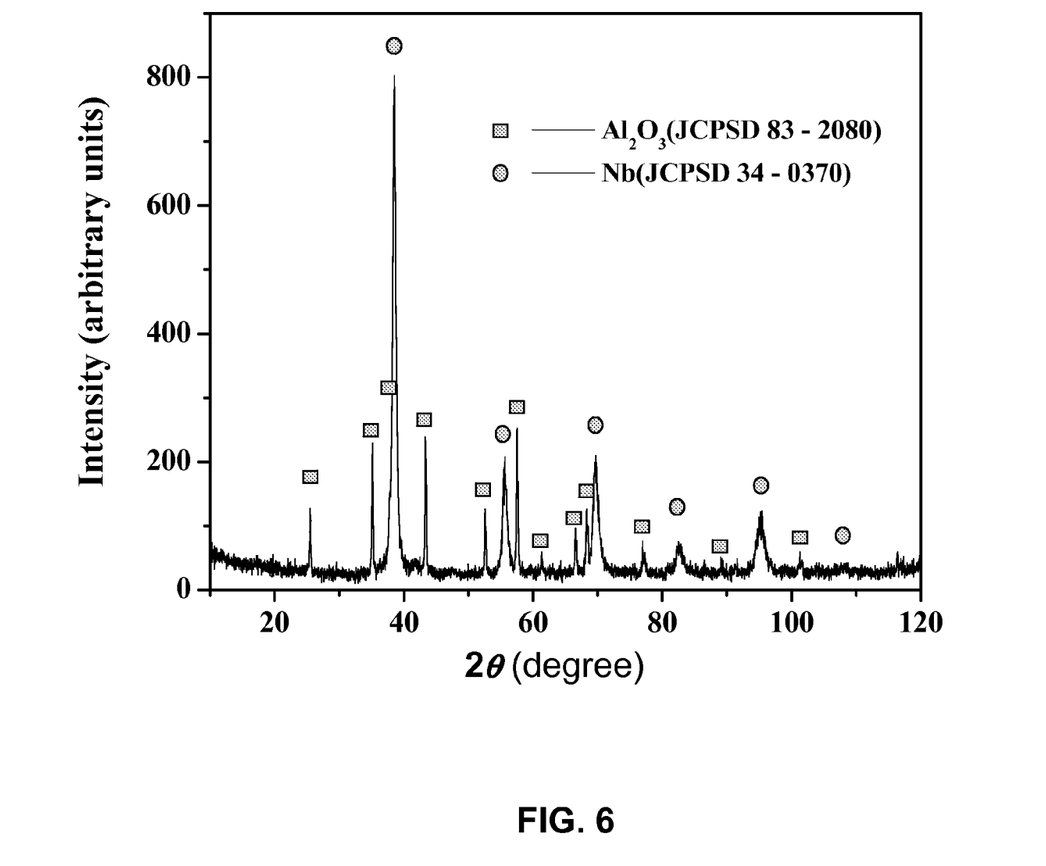
FIG. 6 is a graph showing the XRD pattern of the boundary between the Nb core and the innermost transition layer of an $Al_2O_3/Nb$ laminated composite as measured in Example 2.

To verify that no chemical reaction occurred between the materials comprising the composite, the composite material sample was subjected to XRD detection (Model D/mas 2550 v; Rigaku, Japan), Cu $K_\alpha$ radiation ($\lambda$=0.154056 nm)) at a scanning rate of 1.8°/min in the 2θ range of 10°-120°. FIG. 6 shows the XRD pattern of the boundary between the Nb core and the innermost transition layer. The main diffraction peaks in the XRD pattern corresponded only to those of standard Nb (JCPSD 34-0370) and $Al_2O_3$ (JCPSD 83-2080), indicating that niobium and alumina did not measurably react during the fabrication of the composite material.

The results of this study indicated that the alumina-niobium composite material was characterized by stepwise graded layers with no third phase formation, with continuous distribution of phases between layers, indicating strong bonding between layers.

Example 3

Figure 7:
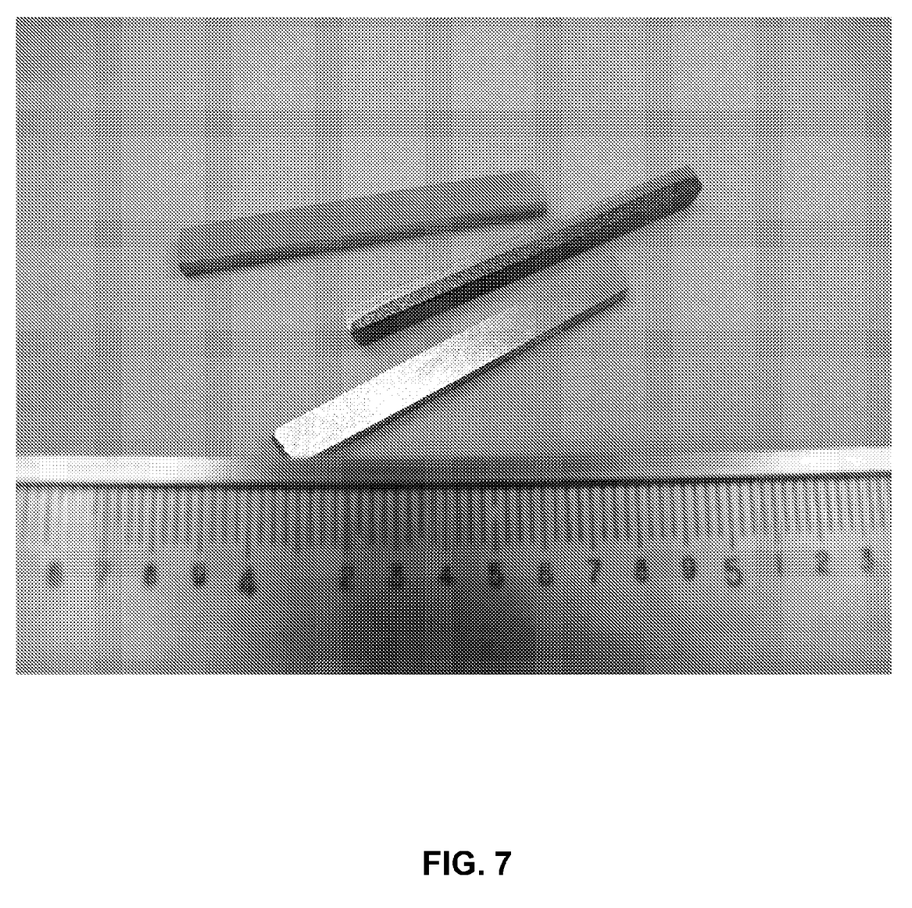
FIG. 7 is a photograph showing the $Al_2O_3/Nb$ composite material samples tested in Example 3.

The Flexural Strength of the Graded Alumina-Niobium Laminated Composite Material was Measured To determine the flexural strength of the alumina-niobium functionally graded composite material, the following experiment was conducted. Alumina-niobium composite material samples fabricated in a disc shape using the methods described in Example 1 were sectioned into rectangular beams, taken parallel to the sample surface to which the external pressure was applied, using a diamond saw. Beams were machined to lengths of about 25 mm, thicknesses of about 1.8 mm and widths of about 2.0 mm, as shown as FIG. 7. The sample surfaces were polished with 1200 grit fine granules of SiC. The four long edges of each sample were uniformly chamfered at 45°, to a depth of 0.12 mm. Measurements were obtained using three samples for each strength test, and average values were calculated.

The flexural strength of the composite material samples was tested using four-point bending with an inner span of 10 mm and an outer span of 20 mm. The flexural strength was measured according to the ASTM standard of C1161-02c at a crosshead speed of 0.2 mm/min. The flexural strength (S) was calculated according the following equation:

$$S = \frac{3PL}{4bd^2}, \quad \text{Eq. (1)}$$

where P is the load at fracture, L=20 mm is the outer (support) span, b is the sample width and d is the sample thickness.

Young's modulus (E) was estimated from the linear load-deflection curve under compressive stress obtained during four-point flexure testing, and was calculated according to the equation:

$$E = \frac{0.17mL^3}{4bd^3}, \quad \text{Eq. (2)}$$

where m is the slope of tangent to the initial straight-time portion of the load-deflection curve (N/mm), and L, b, and d are defined as in Eq. (1).

Figure 8:
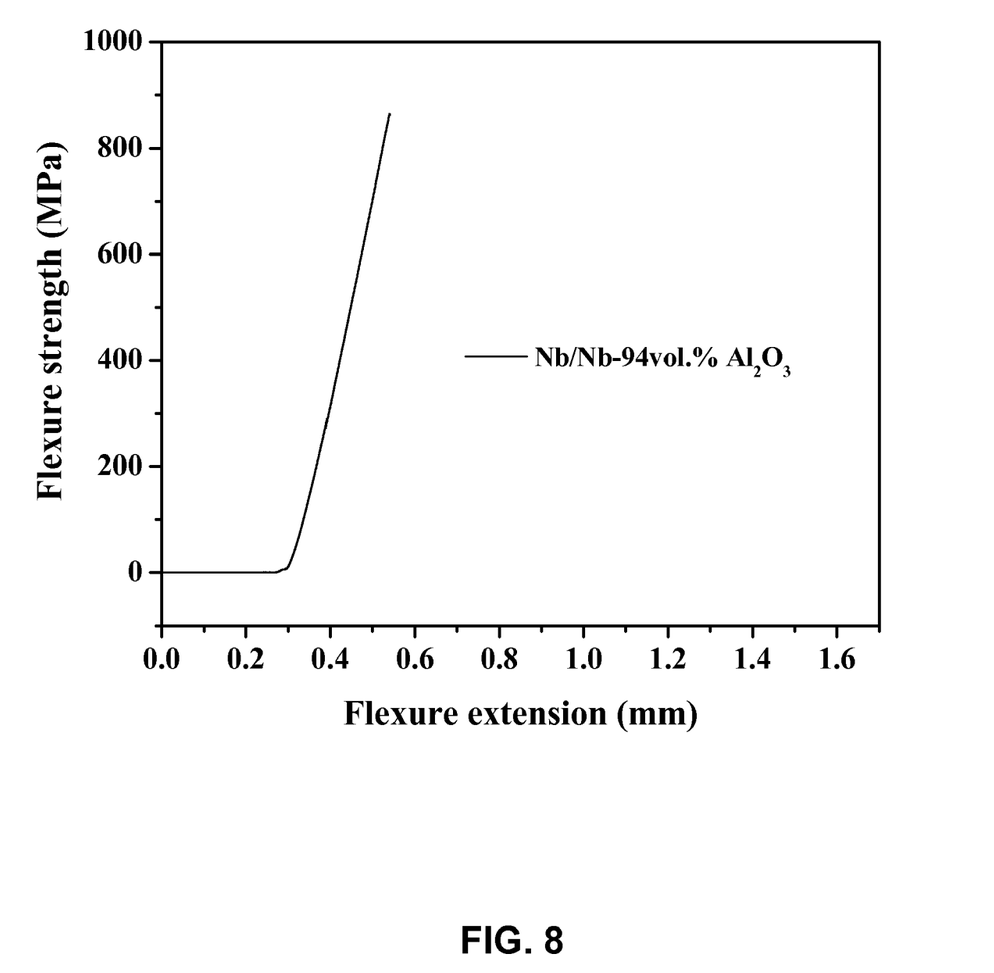
FIG. 8 is a graph showing the flexural stress-displacement curve for a Nb(3Co)/Nb(3Co)-94% $Al_2O_3$ laminated composite as measured in Example 3.
Figure 9:
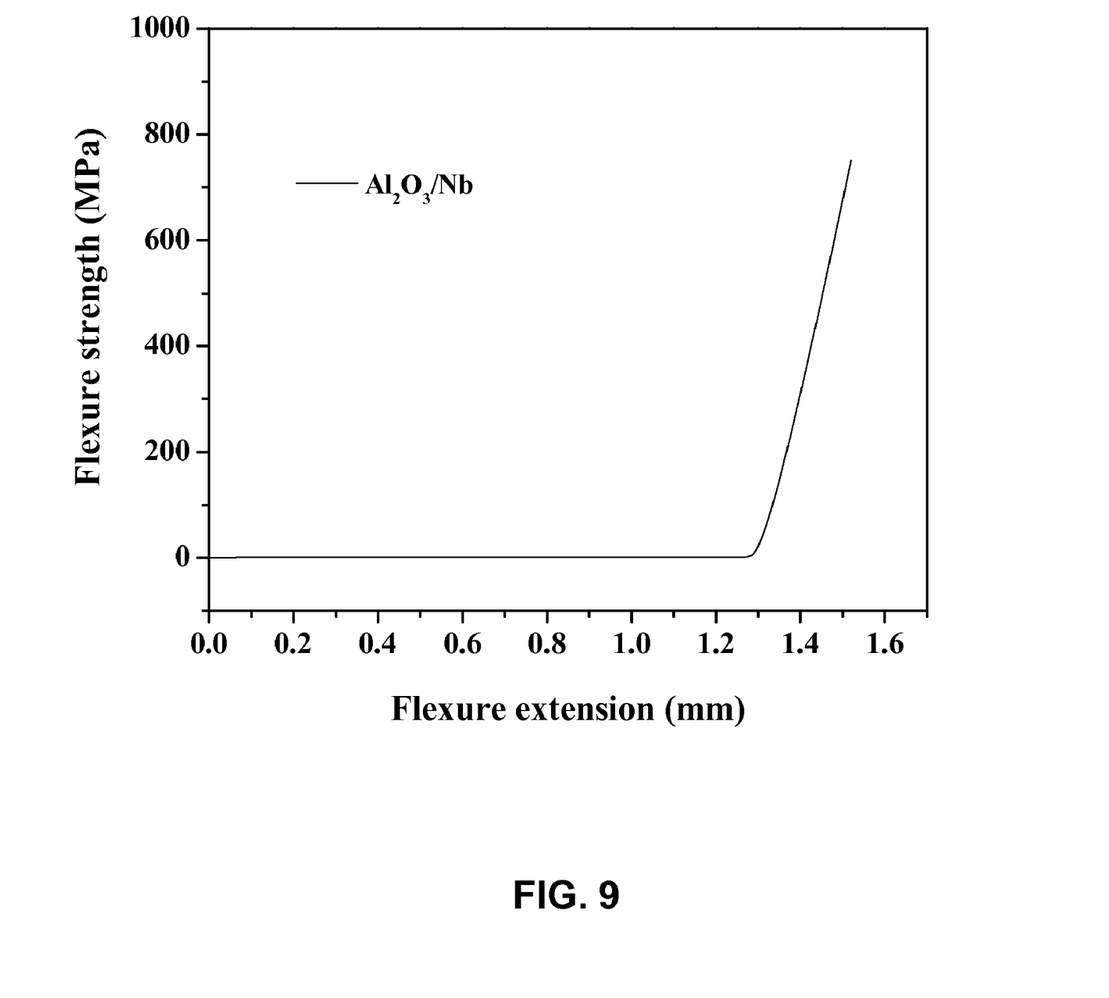
FIG. 9 is a graph showing the flexural stress-displacement curve for a $Al_2O_3/Nb$(3Co) laminated composite sample as measured in Example 3.

FIG. 8 illustrates the flexural stress-displacement curve of the Nb(3Co)/Nb(3Co)-94% $Al_2O_3$ composite sample obtained during flexural testing. FIG. 9 illustrates the flexural stress-displacement curve of the $Al_2O_3$/Nb(3Co) composite sample obtained during flexural testing. Table 1 summarizes the flexural strengths and Young's moduli estimated from the flexural curves obtained during the measurements of the three compositions of composite samples.

TABLE 1

Flexural strength and Young's modulus of three laminated composite samples

| Sample | Sintering condition | Flexural strength/ MPa | Young's modulus/ GPa |
|---|---|---|---|
| Nb/$Al_2O_3$ | 1400° C., 35 MPa, 30 mins | 720 ± 45 | 47.5 ± 2.4 |
| Nb/Nb—94 vol. % $Al_2O_3$ | | 864 ± 50 | 48.3 ± 1.0 |
| $Al_2O_3$/Nb—50 vol. % $Al_2O_3$ | | 704 ± 15 | 55.7 ± 8.1 |
| Nb alone | Reference Values for Comparison | — | 80 – 100 |
| $Al_2O_3$ alone | | 300 – 400 | 350 – 400 |

The data in Table 1 showed that the composites combining $Al_2O_3$ and Nb together possessed higher flexural strengths than the flexural strength of either $Al_2O_3$ or Nb alone. Most likely, the higher strength of the composite material was due to the presence of the ductile Nb layer, which resulted in compressive loading of the $Al_2O_3$ layer. When a crack intersected the Nb/$Al_2O_3$ interface, plastic deformation of the Nb reduced the crack-tip stress intensity, preventing crack propagation through the Nb, thereby delaying the failure of the material samples.

The micro-hardness of the Nb(3Co) particles and $Al_2O_3$ matrix was also determined using a microhardness tester (Tukon microhardness tester, Page-Wilson Corporation) with a 200-gram load. The hardness of Nb(3Co) particles was measured to be 551 kgf/mm$^2$ and the hardness of $Al_2O_3$ was measured to be 3097 kgf/mm$^2$.

The results of this experiment indicated that the $Al_2O_3$—Nb layered composite material exhibited a flexural strength that was higher than either of the two materials in isolation. The addition of the Nb layer to the $Al_2O_3$ enhanced the flexural strength of the resulting material by inhibiting the propagation of cracks that originated in the more brittle, but stiffer $Al_2O_3$ layer.

Example 4

The Fracture Morphologies and Fracture Mechanisms of the Graded Alumina-Niobium Laminated Composite Material was Characterized To determine the fracture morphology of the alumina-niobium functionally graded composite material, the following experiment was conducted. SEM images of alumina-niobium composite samples fabricated as described in Example 1 were obtained to visualize the distribution and patterning of cracks formed in the material samples during flexural strength testing as described in Example 3.

Figure 10:
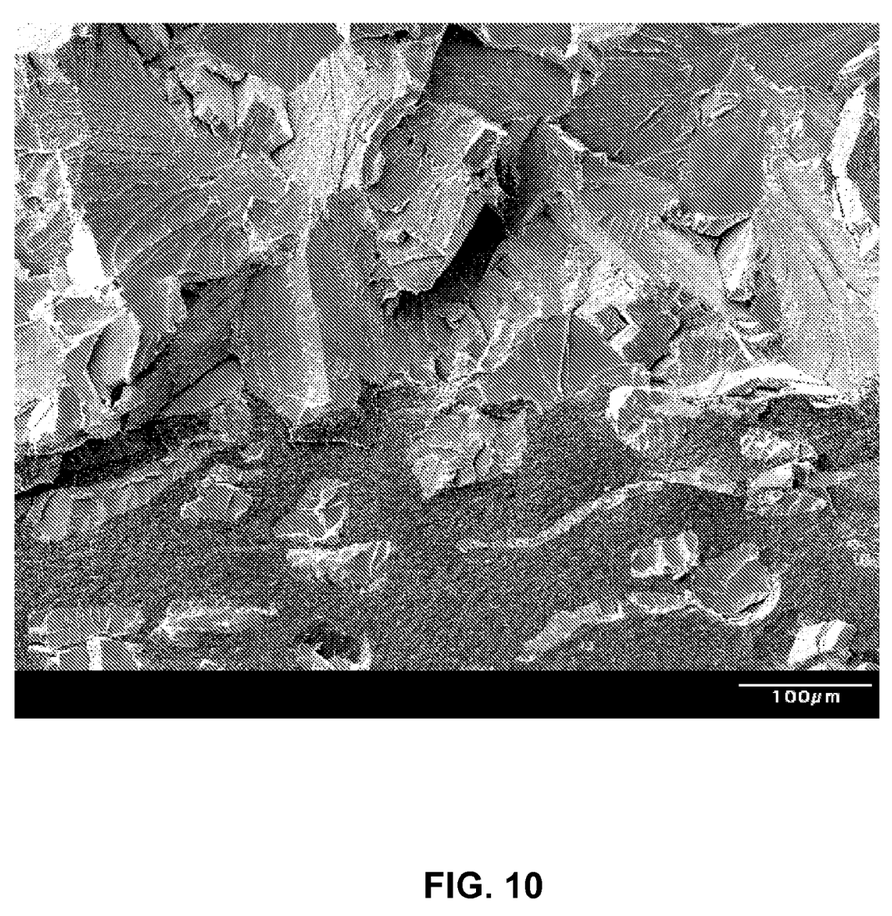
FIG. 10 is an SEM image showing the flexural fracture morphology of a laminated Nb/Nb-94 vol. % $Al_2O_3$ composite.
Figure 11:
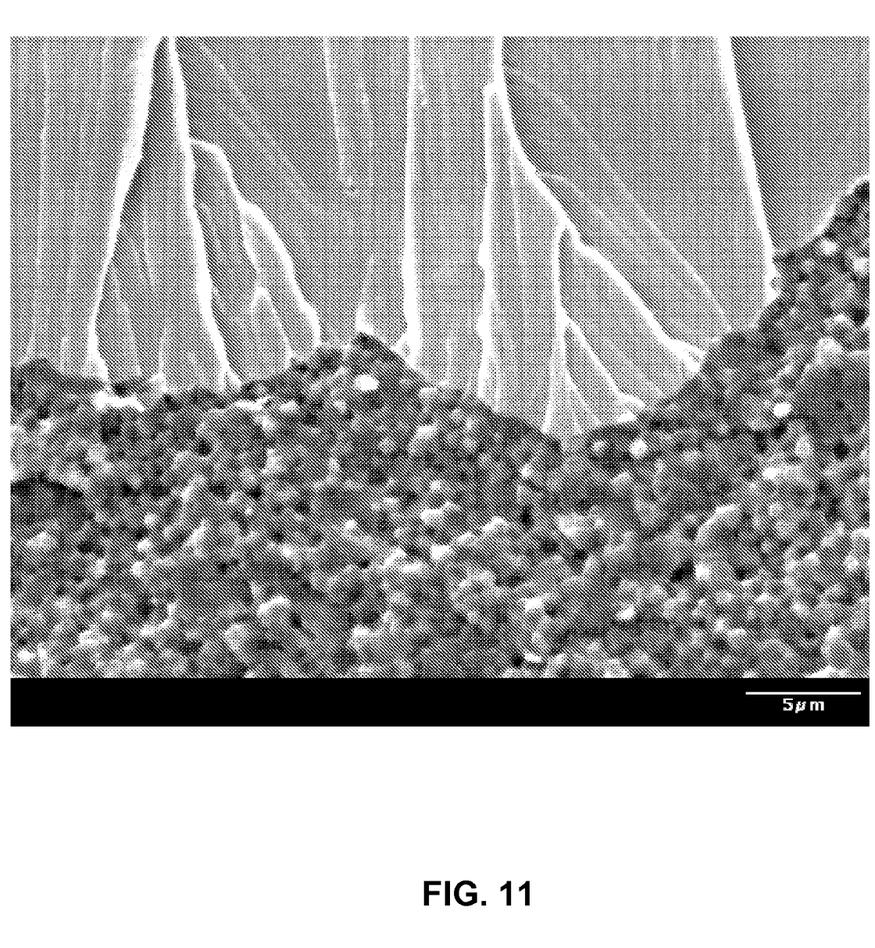

FIG. 10 is an SEM image of the flexural fracture morphology of a laminated Nb/Nb-94 vol. % $Al_2O_3$ composite and FIG. 11 is a similar SEM image of the laminated $Al_2O_3$/Nb composite. Both FIG. 10 and FIG. 11 show that there was good bonding on the interface between the Nb and the $Al_2O_3$ phases, with negligible delamination of the composite layers during flexural fracture. The higher magnification SEM image of the interface between the $Al_2O_3$ and Nb layers in FIG. 10 clearly showed that the cracks generated during flexural fracture did not propagate along the interface between $Al_2O_3$/Nb phases because of the very strong bond of the Nb/$Al_2O_3$ phase interface.

The SEM images shown in FIG. 10 and FIG. 11 showed that the cracks propagated through the $Al_2O_3$ layer, but stopped at the interface between $Al_2O_3$ and Nb layers. This crack morphology suggested that the Nb layer possessed a higher fracture toughness because local plastic deformations of the Nb at the tips of cracks reduced the crack-tip stress intensities, inhibiting the propagation of cracks through the Nb-containing layers.

The results of this experiment lent further support to the conclusion that the enhanced fracture toughness of the layered $Al_2O_3$/Nb composite materials was due to the strong bonding between the composite layers, coupled with the ability of the Nb layer to inhibit crack propagation through the material.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An orthopedic implant component comprising:
   a support member comprising a homogeneous metallic species composition;
   an interface layer bonded to the support member, the interface layer comprising:
      a first sub-layer comprising between about 5% and about 95% of a ceramic material and between about 95% and about 5% of a metal material by volume;
      a second sub-layer comprising between about 5% and about 95% of a ceramic material and between about 95% and about 5% of a metal material by volume; and
      a third sub-layer comprising between about 5% and about 95% of a ceramic material and between about 95% and about 5% of a metal material by volume; and,
   an outermost surface layer of a ceramic composition bonded to the interface layer opposite the support member, the ceramic composition comprised of a ceramic material and a metallic species, whereby the thickness of the ceramic composition layer ranges between about 200 microns and about 10 mm.

2. The implant component of claim 1, wherein the ceramic material is selected from the group consisting of alumina, zirconia, chromium carbide, chromium nitride, silicon carbide, silicon nitride, titanium carbide, zirconium carbide, zirconium nitride, tantalum carbide, tungsten carbide, and any combination thereof.

3. The implant component of claim 1, wherein the metallic species is selected from the group consisting of Nb, Zr, Ti, Ta, Co, V, Cr, Al, alloys thereof, stainless steel, and combinations thereof.

* * * * *